(12) United States Patent
Shimada et al.

(10) Patent No.: US 10,888,291 B2
(45) Date of Patent: Jan. 12, 2021

(54) BREAST IMAGING DEVICE, IMAGE PROCESSING DEVICE, AND IMAGE PROCESSING METHOD

(71) Applicant: CANON KABUSHIKI KAISHA, Tokyo (JP)

(72) Inventors: Tetsuo Shimada, Hachioji (JP); Osamu Tsujii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 78 days.

(21) Appl. No.: 16/117,243

(22) Filed: Aug. 30, 2018

(65) Prior Publication Data

US 2019/0083051 A1    Mar. 21, 2019

(30) Foreign Application Priority Data

Sep. 19, 2017  (JP) ................................ 2017-179105

(51) Int. Cl.
  *A61B 6/00*  (2006.01)
  *A61B 6/03*  (2006.01)
  *A61B 6/04*  (2006.01)

(52) U.S. Cl.
  CPC .............. *A61B 6/502* (2013.01); *A61B 6/032* (2013.01); *A61B 6/0414* (2013.01); *A61B 6/4417* (2013.01); *A61B 6/465* (2013.01); *A61B 6/5235* (2013.01)

(58) Field of Classification Search
  CPC ....... A61B 6/502; A61B 6/032; A61B 6/0414; A61B 6/4417; A61B 6/465; A61B 6/5235
  See application file for complete search history.

(56) References Cited

U.S. PATENT DOCUMENTS

| 7,024,028 | B1* | 4/2006 | Bar Shalev | G06T 19/00 345/422 |
| 2006/0262898 | A1* | 11/2006 | Partain | A61B 6/502 378/37 |
| 2014/0219416 | A1* | 8/2014 | Kimoto | G06T 11/003 378/8 |
| 2017/0294016 | A1* | 10/2017 | Lee | G06T 11/005 |

FOREIGN PATENT DOCUMENTS

| JP | H06-189952 A | 7/1994 |
| JP | 2010-68929 A | 4/2010 |
| JP | 2012-011255 A | 1/2012 |
| JP | 2014-68752 A | 4/2014 |
| WO | 2009/107770 A1 | 9/2009 |

* cited by examiner

*Primary Examiner* — Khai M Nguyen
(74) *Attorney, Agent, or Firm* — Canon U.S.A., Inc. IP Division

(57) ABSTRACT

A breast imaging device for rotating a radiation detection unit configured to detect radiation irradiated from a radiation generation unit configured to generate the radiation with the radiation detection unit and the radiation generation unit facing each other includes a ray sum image generation unit configured to generate a ray sum image based on an addition value of at least one pixel value in a visual line direction from volume data reconstructed from a projection image output from the radiation detection unit, a maximum intensity projection image generation unit configured to generate a maximum intensity projection image based on the maximum pixel value in the visual line direction from the volume data, and a synthesizing unit configured to synthesize the ray sum image and the maximum intensity projection image.

11 Claims, 13 Drawing Sheets

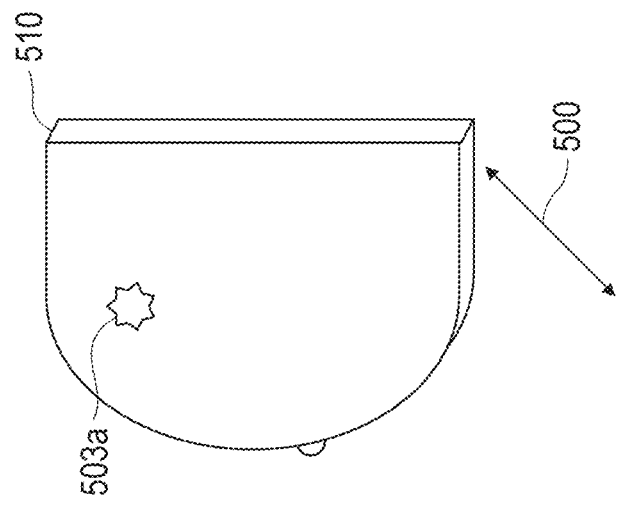
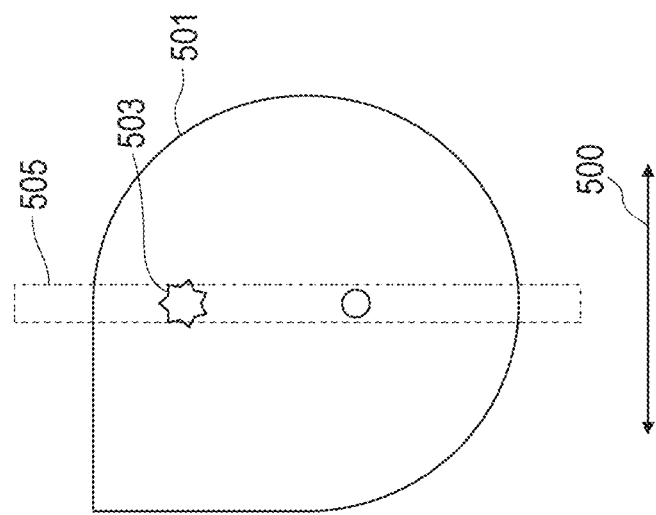

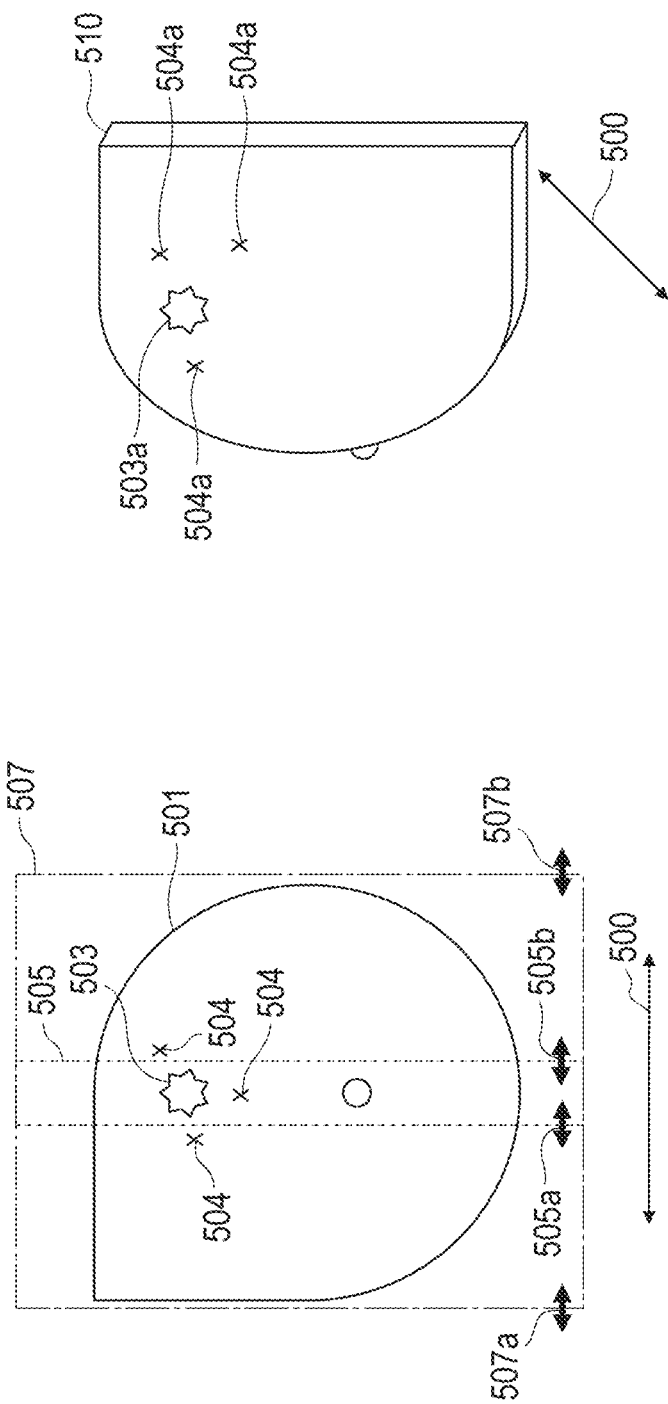

BREAST IMAGING DEVICE, IMAGE PROCESSING DEVICE, AND IMAGE PROCESSING METHOD

BACKGROUND

Field of the Disclosure

The present disclosure relates to a breast imaging device configured to extract and display a specific tissue from an image acquired by breast imaging, an image processing device, and an image processing method.

Description of the Related Art

There is a breast imaging device configured to rotate, by a rotation unit, a radiation generation unit configured to generate radiation and a radiation detection unit configured to detect the radiation, thereby imaging the breast. A CT device (e.g., Japanese Patent Laid-Open No. 2010-68929) has been disclosed, which is configured such that a radiation generation unit and a radiation detection unit arranged to sandwich a rotational shaft passing through an opening into which the breast is inserted are rotated about the rotational shaft. A technique (e.g., Japanese Patent Laid-Open No. 2014-68752) has been disclosed, in which synthesizing processing is performed after multiple types of processing have been performed with different slice thicknesses by means of a three-dimensional image acquired by a tomosynthesis device.

The three-dimensional images described in Japanese Patent Laid-Open No. 2010-68929 and Japanese Patent Laid-Open No. 2014-68752 might include specific tissues (e.g., a tumor tissue, a minute calcified tissue). However, no three-dimensional image is displayed such that each tissue is easily observed.

SUMMARY

An object of the present disclosure is to provide a breast imaging device configured to display a three-dimensional image such that each of specific tissues is easily observed, an image processing device, and an image processing method.

For accomplishing the objective of the present disclosure, a breast imaging device for rotating a radiation detection unit configured to detect radiation irradiated from a radiation generation unit configured to generate the radiation with the radiation detection unit and the radiation generation unit facing each other includes a ray sum image generation unit configured to generate a ray sum image based on an addition value of at least one pixel value in a visual line direction from volume data reconstructed from a projection image output from the radiation detection unit, a maximum intensity projection image generation unit configured to generate a maximum intensity projection image based on the maximum pixel value in the visual line direction from the volume data, and a synthesizing unit configured to synthesize the ray sum image and the maximum intensity projection image.

Further features of the present invention will become apparent from the following description of exemplary embodiments (with reference to the attached drawings).

BRIEF DESCRIPTION OF THE DRAWINGS

FIGS. 11A and 11B are views of one display form of the display unit of the present invention.

FIGS. 13A and 13B are views of one display form of the display unit of the present invention.

DESCRIPTION OF THE EMBODIMENTS

Figure 1:
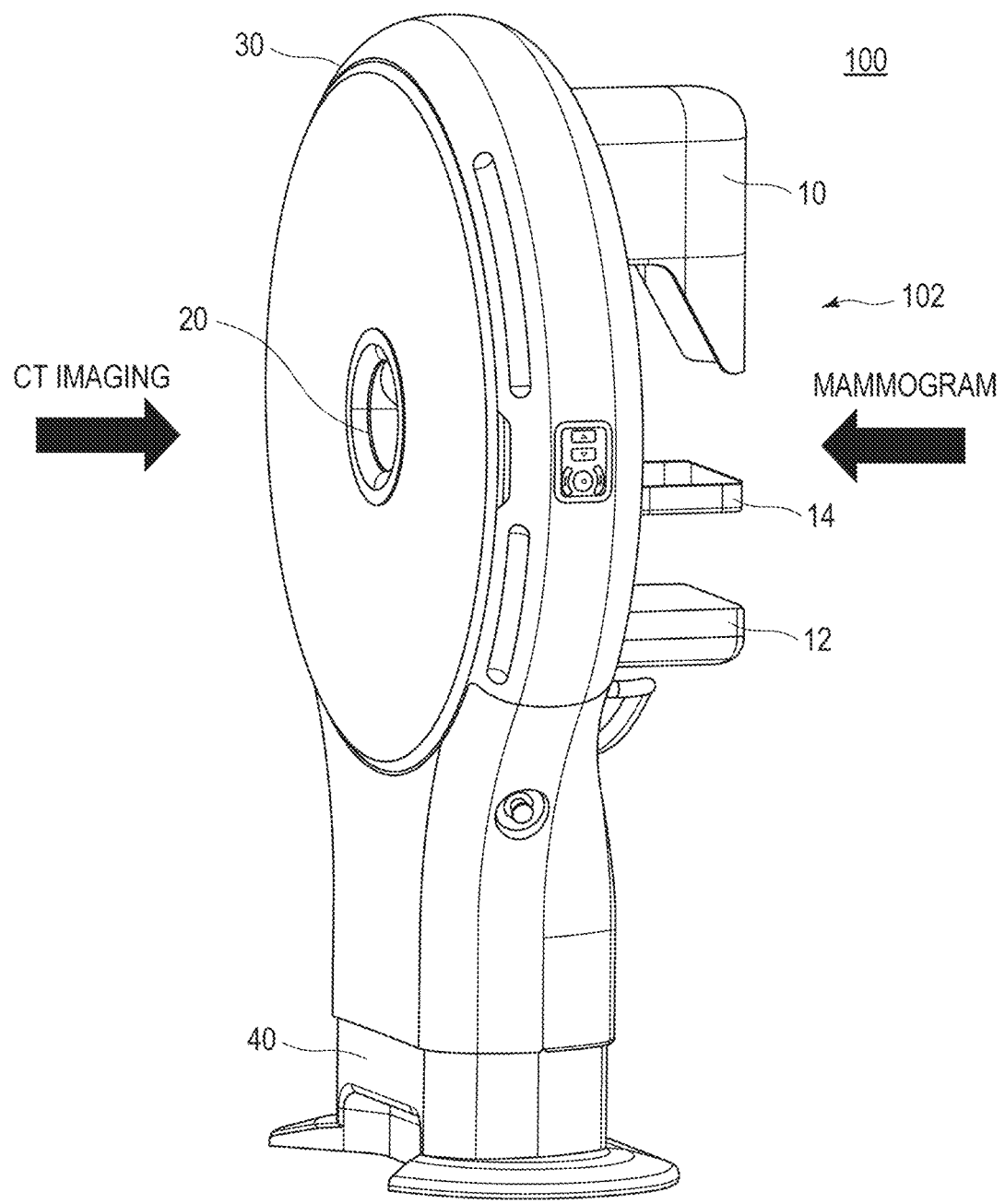
FIG. 1 is a view of an outer appearance of a breast imaging device of the present invention.

FIG. 1 is a view of an outer appearance of a breast imaging device 100. The breast imaging device 100 can perform mammogram and CT imaging. Upon mammogram and CT imaging, a subject is at a standing position. The standing position is a state in which the subject stands on a floor surface with both feet of the subject being on the floor surface.

The breast imaging device 100 can rotate a radiation generation unit 10 configured to generate radiation and a radiation detection unit 12 configured to detect the radiation irradiated from the radiation generation unit 10 in a state in which the radiation generation unit 10 and the radiation detection unit 12 face each other. An imaging unit 102 mainly includes the radiation generation unit 10 and the radiation detection unit 12.

An imaging target portion (the breast) of the subject is imaged from a first side of the breast imaging device 100 with the imaging target portion being sandwiched between a pressing plate 14 and the radiation detection unit 12. That is, the breast imaging device 100 has a mammogram mode. Then, the imaging target portion (the breast) of the subject is imaged from a second side opposite to the first side of the breast imaging device 100 in such a manner that the radiation generation unit 10 and the radiation detection unit 12 are rotated with the imaging target portion being inserted to between the radiation generation unit 10 and the radiation detection unit 12 and being placed on a breast cup. That is, the breast imaging device 100 has a CT imaging mode.

In the case of performing mammogram, the imaging target portion (the breast) of the subject is imaged from the first side (the right side as viewed in the figure) of the breast imaging device 100 with the imaging target portion being sandwiched between the pressing plate 14 and the radiation detection unit 12. The pressing plate 14 is made of a transparent material through which the radiation is transmitted. Specifically, the pressing plate 14 is moved up and down so that the breast of the subject can be sandwiched between the pressing plate 14 and the radiation detection unit 12. The radiation is generated by the radiation generation unit 10 with the breast of the subject being sandwiched between the pressing plate 14 and the radiation detection unit 12. The radiation detection unit 12 detects the radiation having been transmitted through the breast of the subject so that the breast of the subject can be imaged. The breast imaging device 100 can generate a mammogram image based on imaged radiation data.

In the case of performing CT imaging, the imaging target portion (the breast) of the subject is, from the second side (the left side as viewed in the figure) opposite to the first side of the breast imaging device 100, inserted to between the radiation generation unit 10 and the radiation detection unit 12. Then, in this state, imaging is performed in such a manner that the radiation generation unit 10 and the radiation detection unit 12 are rotated by a rotation frame 38. Specifically, an opening 20 for insertion of the breast of the subject is provided at a gantry 30 of the breast imaging device 100. In a state in which the breast of the subject is inserted into the opening 20 and is placed on the breast cup, imaging is performed in such a manner that the radiation generation unit 10 and the radiation detection unit 12 are rotated by the rotation frame 38. While the radiation generation unit 10 and the radiation detection unit 12 are being rotated by the rotation frame 38, the radiation is generated by the radiation generation unit 10. The radiation detection unit 12 detects the radiation having been transmitted through the breast of the subject so that the breast of the subject can be imaged. The breast imaging device 100 reconstructs the imaged radiation data so that a CT image can be generated.

The first side of the breast imaging device 100 is a mammogram side, and the second side of the breast imaging device 100 is a CT imaging side. A line horizontally connecting the first side (the mammogram side) and the second side (the CT imaging side) is substantially parallel to a rotation axis of the rotation frame 38. Moreover, the line horizontally connecting the first side (the mammogram side) and the second side (the CT imaging side) is perpendicular to the plane of the substantially flat plate-shaped gantry 30 or the plane of a front cover 26.

The first side (the mammogram side) and the second side (the CT imaging side) of the breast imaging device 100 are regions divided by the substantially flat plate-shaped gantry 30, the front cover 26, and the imaging unit 102 of the breast imaging device 100.

Figure 2:
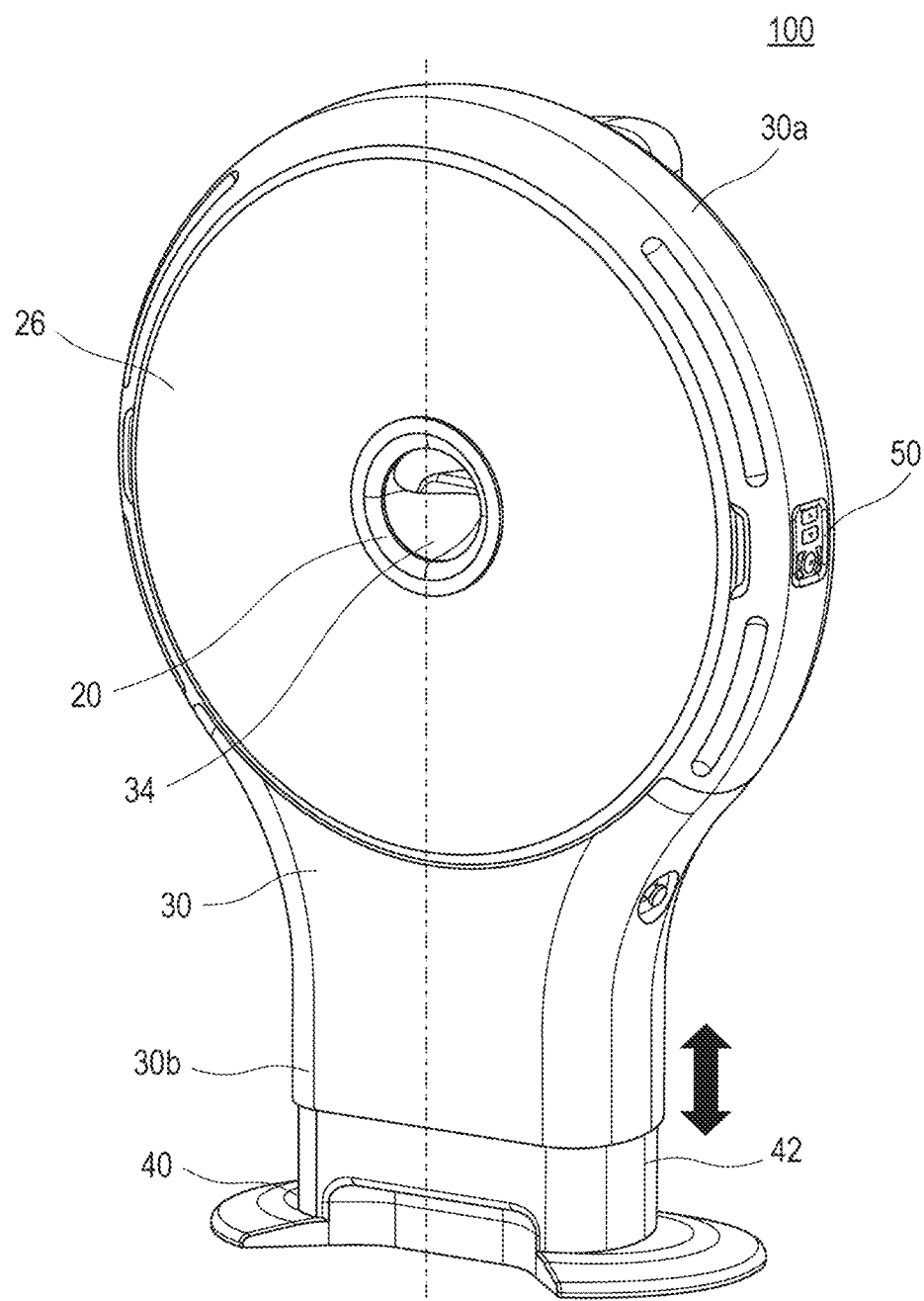
FIG. 2 is a view of the outer appearance of the breast imaging device of the present invention from a CT imaging side.
Figure 3:
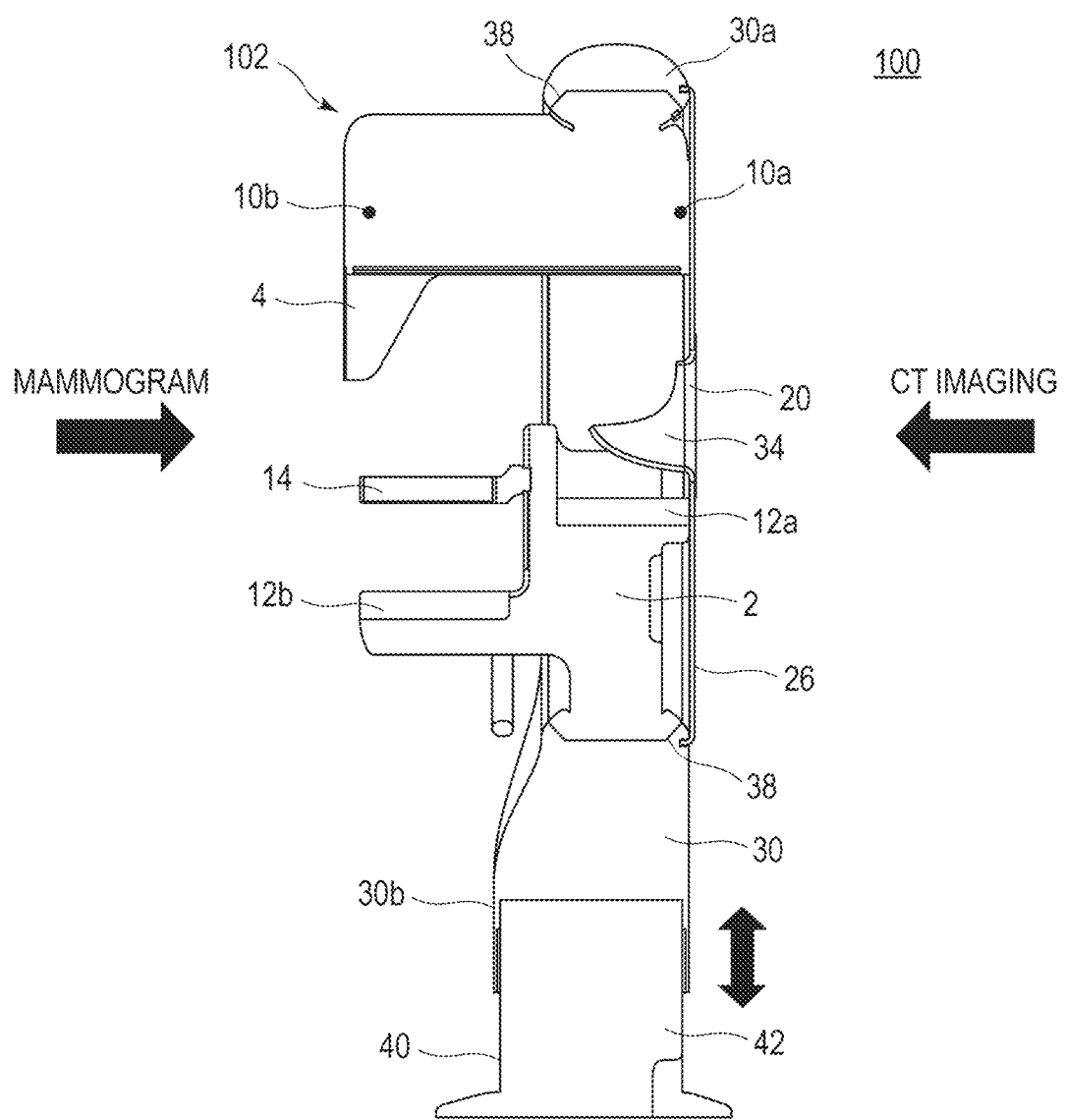
FIG. 3 is a sectional view of the breast imaging device of the present invention.
Figure 4:
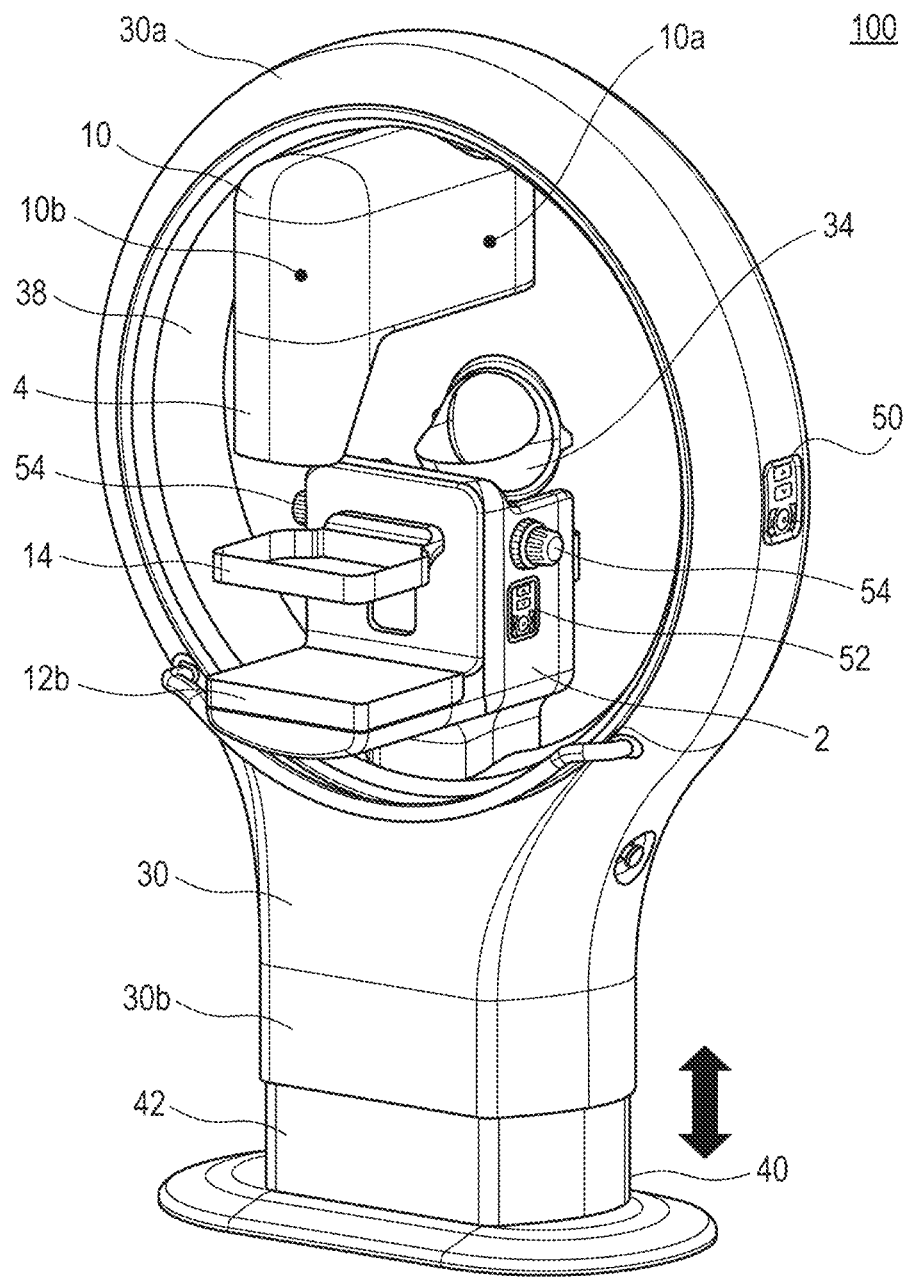
FIG. 4 is a view of the outer appearance of the breast imaging device of the present invention from a mammogram side.

The breast imaging device 100 will be specifically described with reference to FIGS. 2 to 4. FIG. 2 is a view of the outer appearance of the breast imaging device 100 from the CT imaging side. FIG. 3 is a sectional view of the breast imaging device 100. The sectional view of the breast imaging device 100 is a sectional view along a center line (a chain line) of the breast imaging device 100 of FIG. 2 extending in the vertical direction. FIG. 4 is a view of the outer appearance of the breast imaging device 100 from the mammogram side.

As illustrated in FIG. 2, the front cover 26 configured to protect the subject from the radiation generation unit 10 and the radiation detection unit 12 to be rotated upon CT imaging is placed at the gantry 30 on the CT imaging side. The front cover 26 has the opening 20 for insertion of the breast of the subject for CT imaging, and the breast cup 34 is placed borderlessly and continuously from the opening 20.

As illustrated in FIG. 4, the pressing plate 14 configured to press the breast of the subject for mammogram is placed at the gantry 30 on the mammogram side. Moreover, a protection plate 4 configured to protect the subject from unnecessary exposure is placed at the gantry 30 on the mammogram side.

Figure 5:
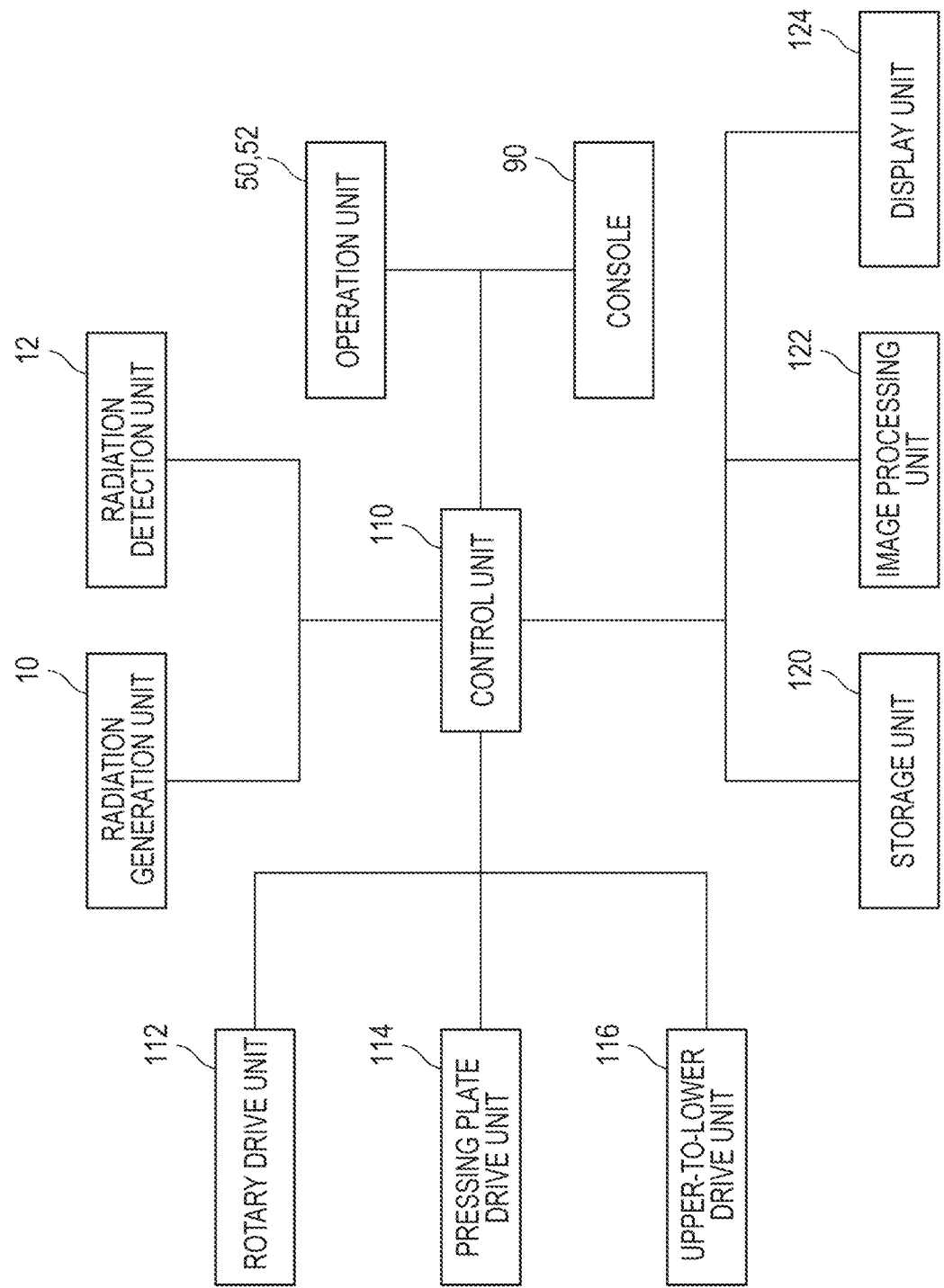
FIG. 5 is a diagram of a configuration of the breast imaging device of the present invention.

FIG. 5 illustrates a configuration diagram of the breast imaging device 100. The breast imaging device 100 includes a rotary drive unit 112 configured to rotate the radiation generation unit 10 and the radiation detection unit 12 with the radiation generation unit 10 and the radiation detection unit 12 facing each other. Moreover, the breast imaging device 100 includes a pressing plate drive unit 114 configured to move the pressing plate 14 up and down, and an upper-to-lower drive unit 116 configured to move the gantry 30 up and down relative to a support leg 40.

The breast imaging device 100 includes a control unit 110 configured to control each of the radiation generation unit 10, the radiation detection unit 12, the rotary drive unit 112, the pressing plate drive unit 114, and the upper-to-lower drive unit 116. Moreover, the breast imaging device 100 includes operation units 50, 52 and a console 90 configured to transfer an instruction to the control unit 110. The operation unit 50 configured to operate the breast imaging device 100 is placed at the gantry 30, and the operation unit 52 having the same function as that of the operation unit 50 is placed at a support base 2 configured to support the radiation detection unit 12. Moreover, the console 90 is placed outside an imaging room.

Moreover, the breast imaging device 100 includes a storage unit 120 configured to store an image such as a projection image, a tomographic image, or a three-dimensional image including multiple tomographic images, an image processing unit 122 configured to generate a tomographic image as a two-dimensional image and a three-dimensional image from volume data acquired by reconstruction of multiple projection images, and a display unit 124 configured to display a tomographic image or a three-dimensional image. A projection image acquired from the radiation detection unit 12 is stored in the storage unit 120. Then, the image processing unit 122 reads and reconstructs multiple projection images, and converts these images into the volume data. Then, the storage unit 120 stores the volume data reconstructed by the image processing unit 122. The display unit 124 reads, according to an operator's instruction, the volume data from the storage unit 120, and displays a tomographic image. The display unit 124 can also display a three-dimensional image.

Although not shown in the figure, the radiation generation unit 10 mainly includes an electron emitting source configured to generate electrons and a target. The electrons generated from the electron emitting source are emitted to a target side by a potential difference between a cathode and an anode. The target is a member configured to generate radiation due to electron collision. The radiation emitted from the target is shaped in a cone-beam shape, and is irradiated to the outside. The control unit 110 can control an imaging condition of the radiation generation unit 10.

The radiation detection unit 12 is configured to detect, by a photoelectric conversion element, the radiation having been transmitted through the subject, thereby outputting the radiation as an electric signal. For example, the radiation detection unit 12 includes a conversion panel configured to detect the radiation having been transmitted through the subject, an electric storage unit, and an interface (I/F) for outputting information converted from the radiation into the electric signal. By the interface (I/F), the electric signal is output to the control unit 110.

As illustrated in FIGS. 2 to 4, the gantry 30 has the ring-shaped rotation frame 38 for rotating the radiation generation unit 10 and the radiation detection unit 12 with the radiation generation unit 10 and the radiation detection unit 12 facing each other, and a ring-shaped fixed frame 30a configured to rotatably support the rotation frame 38. Moreover, the gantry 30 has an elongated cylindrical portion 30b coupled to the fixed frame 30a and formed in an elongated cylindrical shape. The rotation frame 38 and the fixed frame 30a can be referred to as a rotation unit configured to rotate the radiation generation unit 10 and the radiation detection unit 12. The fixed frame 30a and the elongated cylindrical portion 30b are integrally formed. The fixed frame 30a is positioned above the elongated cylindrical portion 30b. The elongated cylindrical portion 30b is coupled to the support leg 40 configured to support the gantry 30 on the floor surface.

The gantry 30 stands in the vertical direction so that the subject can perform imaging at the standing position. A rotation axis of the rotation unit (the rotation frame 38 at the gantry 30) configured to rotate the radiation generation unit 10 and the radiation detection unit 12 is in the horizontal direction.

The elongated cylindrical portion 30b covers the outer periphery of an elongated cylindrical portion 42 of the support leg 40. That is, the elongated cylindrical portion 42 of the support leg 40 is assembled into the elongated cylindrical portion 30b of the gantry 30, and the elongated cylindrical portion 42 of the support leg 40 and the elongated cylindrical portion 30b of the gantry 30 form a nested structure.

The breast imaging device 100 includes the upper-to-lower drive unit 116 configured to move the elongated cylindrical portion 30b up and down relative to the support leg 40, and therefore, can adjust the height of the opening 20 in accordance with the body type of the subject.

The breast imaging device 100 includes the radiation generation unit 10 configured to generate the radiation and the radiation detection unit 12 configured to detect the radiation irradiated from the radiation generation unit 10, and therefore, can rotate the radiation generation unit 10 and the radiation detection unit 12 with the radiation generation unit 10 and the radiation detection unit 12 facing each other.

The radiation generation unit 10 and the radiation detection unit 12 are placed on the rotation frame 38 configured to rotate relative to the fixed frame 30a of the gantry 30. As illustrated in FIG. 3, the breast imaging device 100 includes a radiation generation unit 10a and a radiation detection unit 12a for CT imaging, and a radiation generation unit 10b and a radiation detection unit 12b for mammogram. The gantry 30 includes the radiation generation unit 10a and the radiation detection unit 12a for CT imaging, and the radiation generation unit 10b and the radiation detection unit 12b for mammogram. That is, the breast imaging device 100 includes two groups of the radiation generation units and the radiation detection units for CT imaging and mammogram.

The gantry 30 has the ring-shaped rotation frame 38 for rotation in a state in which the radiation generation unit 10a and the radiation detection unit 12a for CT imaging face each other and the radiation generation unit 10b and the radiation detection unit 12b for mammogram face each other.

Specifically, for CT imaging, the radiation generation unit 10a and the radiation detection unit 12a are placed at the rotation frame 38. The radiation detection unit 12a is placed at the rotation frame 38 through the support base 2 configured to support the radiation detection unit 12a.

For mammogram, the radiation generation unit 10b and the radiation detection unit 12b are placed at the rotation frame 38. The radiation detection unit 12b is placed at the rotation frame 38 through the support base 2.

The rotation frame 38 is coupled to the fixed frame 30a of the gantry 30 through a bearing having a bearing structure. The fixed frame 30a is a stationary frame in an unmoved state. The rotation frame 38 can be rotated by the rotary drive unit 112. The rotary drive unit 112 is placed in the gantry 30 such that the rotation axis of the rotation frame 38 is in the horizontal direction.

Moreover, the pressing plate 14 is placed at the support base 2 such that upper-to-lower movement of the pressing plate 14 is allowed. Further, a rotation tab 54 configured to move the pressing plate 14 up and down is placed at the support base 2. The rotation tab 54 is rotated to lower the pressing plate 14 so that the breast of the subject can be sandwiched between the pressing plate 14 and the radiation detection unit 12b.

As described above, the support base 2 is placed at the rotation frame 38 to support the radiation detection unit 12a, the radiation detection unit 12b, and the pressing plate 14. The rotation frame 38 is, together with the support base 2, rotated by the rotary drive unit 112 so that the radiation detection unit 12a and the radiation detection unit 12b can be rotated. Moreover, the rotation frame 38 is rotated by the rotary drive unit 112 so that the radiation generation unit 10a and the radiation generation unit 10b can be rotated.

As illustrated in FIG. 3, the radiation generation unit 10a and the radiation generation unit 10b are placed at the substantially same height. The radiation detection unit 12a is placed at a position higher than the radiation detection unit 12b.

In other words, the radiation generation unit 10a and the radiation generation unit 10b are placed to be at the same position (the same distance) with respect to the rotation axis of the rotation unit (the rotation frame 38).

Moreover, the radiation detection unit 12a and the radiation detection unit 12b are placed such that the radiation detection unit 12b is positioned on the outside than the radiation detection unit 12a with respect to the rotation axis of the rotation unit (the rotation frame 38).

A distance between the radiation generation unit 10a and the radiation detection unit 12a used upon CT imaging is shorter than a distance between the radiation generation unit 10b and the radiation detection unit 12b upon mammogram.

Upon mammogram, the breast of the subject is sandwiched between the pressing plate 14 and the radiation detection unit 12b. The breast of the subject is compressed into a flat plate shape by pressing, and therefore, an area to be irradiated with radiation needs to be increased to ensure a field of view (FOV: an irradiation field). Thus, the radiation detection unit 12b used upon mammogram is placed at a position lower than the radiation detection unit 12a used for CT imaging.

The irradiation field 8 is an irradiation field by the radiation generation unit 10b for mammogram. The radiation generation unit 10b and the radiation detection unit 12b are placed such that the irradiation field 8 from the radiation generation unit 10b includes the pressing plate 14. The irradiation field 8 is in a quadrangular pyramid shape (a cone-beam shape) extending from a focal point of the radiation generation unit 10b as a vertex. As illustrated in FIG. 3, one side end (the left side) of the irradiation field 8 is in the vertical direction, and the other end (the right side) of the irradiation field 8 is in a diagonal direction. For imaging the periphery (the axilla) of the breast of the subject, the irradiation field 8 of the radiation generation unit 10b is set such that an end portion (an irradiation field end portion, an irradiation field end surface) of the irradiation field 8 on a subject side (the left side) for mammogram is in the vertical direction.

On the other hand, the radiation generation unit 10*a* and the radiation detection unit 12*a* are placed such that the size of the rotation frame 38 and the size of the entirety of the breast imaging device 100 (the gantry 30) become compact upon CT imaging. Specifically, the radiation generation unit 10*a* and the radiation detection unit 12*a* are placed such that the distance between the radiation generation unit 10*a* and the radiation detection unit 12*a* is shortened as much as possible. The radiation detection unit 12*a* is placed right below the breast holding unit 34. The radiation detection unit 12*a* is placed at such a position that the radiation detection unit 12*a* does not contact the breast holding unit 34 even when the radiation detection unit 12*a* is rotated by the rotation frame 38.

An irradiation field 6 is an irradiation field by the radiation generation unit 10*a* for CT imaging. The breast of the subject targeted for CT imaging is held on the breast holding unit 34, and is not compressed. The radiation generation unit 10*a* and the radiation detection unit 12*a* are placed such that the irradiation field 6 from the radiation generation unit 10*a* includes a tip end portion of the breast holding unit 34.

The irradiation field 6 is in a quadrangular pyramid shape (a cone-beam shape) extending from a focal point of the radiation generation unit 10*a* as a vertex. As illustrated in FIG. 3, one side end (the right side) of the irradiation field 6 is in the vertical direction, and the other end (the left side) of the irradiation field 6 is in a diagonal direction. For imaging the periphery (the axilla) of the breast of the subject, the irradiation field 6 is set such that an end portion (an irradiation field end portion, an irradiation field end surface) of the irradiation field 6 on a subject side (the right side) for CT imaging is in the vertical direction.

As described above, it is set such that the end portion (the irradiation field end portion, the irradiation field end surface) of the irradiation field 8 on the subject side (the left side) for mammogram is in the vertical direction and that the end portion (the irradiation field end portion, the irradiation field end surface) of the irradiation field 6 on the subject side (the right side) for CT imaging is in the vertical direction. In a breast cancer, metastasis to the periphery (the axilla) of the breast might occur. The irradiation field 6 of the radiation generation unit 10*a* for CT imaging and the irradiation field 8 of the radiation generation unit 10*b* for mammogram are set so that the periphery (the axilla) of the breast of the subject can be imaged.

Note that for ensuring the field of view (FOV: the irradiation field) upon CT imaging, the radiation generation unit 10*a* for CT imaging may be placed at a position higher than the radiation generation unit 10*b* for mammogram. Upon CT imaging, the radiation generation unit 10*a* generates the radiation from the focal point while the radiation generation unit 10*a* and the radiation detection unit 12*a* are rotating.

As described above, the breast imaging device 100 of the present invention includes the first radiation generation unit 10*a* configured to generate the radiation, and the second radiation generation unit 10*b* configured to generate the radiation. Moreover, the breast imaging device 100 includes the first radiation detection unit 12*a* configured to detect the radiation irradiated from the first radiation generation unit 10*a*, and the second radiation detection unit 12*b* configured to detect the radiation irradiated from the second radiation generation unit 10*b*.

The imaging target portion of the subject is, from the first side of the breast imaging device 100, imaged using the first radiation generation unit 10*a* and the first radiation detection unit 12*a* with the imaging target portion being sandwiched between the pressing plate 14 and the first radiation detection unit 12*a*. Moreover, the imaging target portion of the subject is, from the second side opposite to the first side of the breast imaging device 100, imaged in such a manner that the second radiation generation unit 10*b* and the second radiation detection unit 12*b* are rotated with the imaging target portion being inserted to between the second radiation generation unit 10*b* and the second radiation detection unit 12*b*.

As described above, the breast imaging device 100 includes two groups of the radiation generation units and the radiation detection units for CT imaging and mammogram. Thus, the field of view (FOV: the irradiation field) suitable for each of the breast of the subject targeted for CT imaging and the breast of the subject targeted for mammogram can be ensured.

The breast imaging device 100 includes the rotary drive unit 112 configured to rotate the radiation generation unit 10 and the radiation detection unit 12 through the rotation frame 38. The radiation generation unit 10 has the radiation generation unit 10*b* for mammogram, and the radiation generation unit 10*a* for CT imaging.

FIG. 4 illustrates a form for performing caranio caudal view (CC: a caranio-caudal direction) mammogram in the breast imaging device 100. The position of the rotation frame 38 is set such that the radiation generation unit 10*b*, the pressing plate 14, and the radiation detection unit 12*b* are arranged in the vertical direction.

The rotation tab 54 is rotated to move the pressing plate 14 so that a distance between the pressing plate 14 and the radiation detection unit 12*b* can be adjusted. By movement of the pressing plate 14, the breast of the subject can be compressed. In CC mammogram illustrated in FIG. 4, the breast arranged between the pressing plate 14 and the radiation detection unit 12*b* is compressed between the pressing plate 14 and the radiation detection unit 12*b*, and then, radiographic imaging is performed for the breast.

The rotary drive unit 112 is placed inside the fixed frame 30*a*. The rotation frame 38 is rotatably connected to the rotary drive unit 112 through a coupling member (e.g., a belt). Moreover, the bearing is set in a clearance between the fixed frame 30*a* and the rotation frame 38. By driving of the rotary drive unit 112, the rotation frame 38 rotates relative to the fixed frame 30*a*.

In the breast imaging device 100, the radiation detection unit 12 detects the radiation having been transmitted through the breast of the subject upon CT imaging, and therefore, CT imaging can be performed for the breast of the subject.

<Image Processing Unit>

Figure 6:
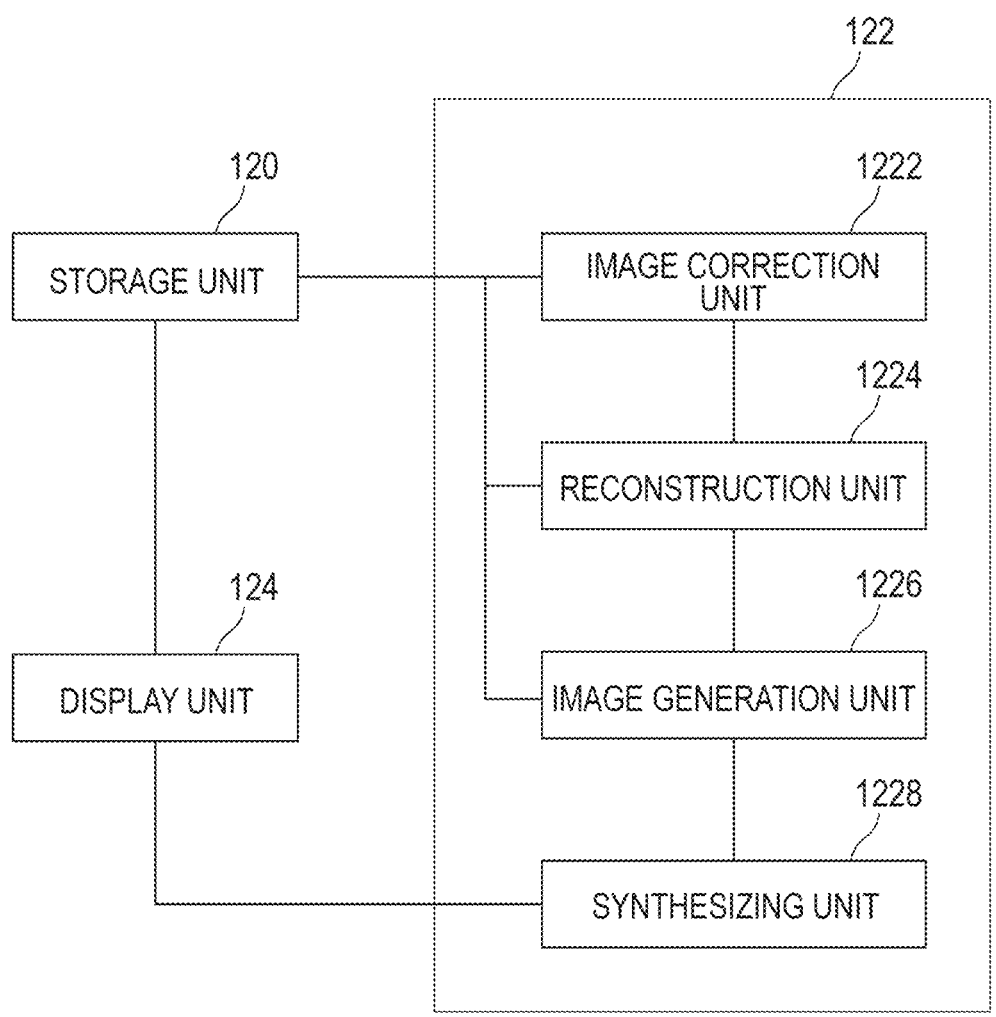
FIG. 6 is a diagram of a configuration of an image processing unit of the present invention.

The image processing unit 122 will be described herein with reference to FIG. 6. FIG. 6 is a diagram of a configuration of the image processing unit 122. The image processing unit 122 has an image correction unit 1222 configured to perform correction of a projection image, a reconstruction unit 1224 configured to reconstruct multiple projection images to generate the volume data, and an image generation unit 1226 configured to generate multiple types of three-dimensional images based on the volume data. Moreover, the image processing unit 122 includes a synthesizing unit 1228 configured to synthesize the multiple types of three-dimensional images. In the present embodiment, the multiple types of three-dimensional images will be mainly described as a ray sum image and a maximum intensity projection image. The synthesizing unit 1228 superimposes the maximum intensity projection image on the ray sum image.

The image correction unit 1222 irradiates the radiation detection unit 12*a* with the radiation from the radiation generation unit 10*a* in a state without the subject, thereby acquiring a gain correction image based on a signal of each pixel. Further, the image correction unit 1222 acquires an offset correction image based on the signal of each pixel of the radiation detection unit 12*a* in a state in which no radiation is irradiated from the radiation generation unit 10*a*. Note that in a case where one or both of the gain correction image and the offset correction image cannot be acquired before imaging of the subject, the image correction unit 1222 may acquire an absent image after imaging of the subject. The image correction unit 1222 uses the gain correction image and the offset correction image to correct a projection image obtained by imaging of the subject, thereby generating a corrected projection image.

The projection image corrected in the image correction unit 1222 is stored in the storage unit 120. Then, the projection image stored in the storage unit 120 is transferred to the reconstruction unit 1224 of the image processing unit 122. The projection image acquired in the radiation detection unit 12*a* may be directly transferred to the reconstruction unit 1224.

The reconstruction unit 1224 reconstructs multiple projection images of the periphery of the breast of the subject output from the radiation detection unit 12*a*, thereby acquiring the volume data. The multiple projection images may be projection images corrected by the image correction unit 1222. A filter correction back projection method, a Feldkamp method in which the filter correction back projection method is applied to multi-slicing, or a successive approximation method has been broadly known as the technique for performing reconstruction, but the present invention does not depend on these reconstruction methods. The volume data reconstructed by the reconstruction unit 1224 is stored in the storage unit 120.

<Image Generation Unit>

The image generation unit 1226 generates the three-dimensional images (the multiple types of images) from the volume data reconstructed in the reconstruction unit 1224. The image generation unit 1226 sets the range (a three-dimensional region) of the volume data on the console 90 so that the three-dimensional images within a predetermined range can be generated. The operator sets, via the console 90, the coordinate range of the volume data such that a target portion (e.g., the mammary gland) of the breast of the subject is displayed. In this manner, the three-dimensional images including the target portion can be generated.

The image generation unit 1226 performs projection processing in a visual line direction for the volume data. Specifically, the image generation unit 1226 adds up all pixel values in the visual line direction in the volume data, thereby generating the sum of the pixel values in the visual line direction as the ray sum image. Moreover, the image generation unit 1226 extracts the maximum pixel value in the visual line direction in the volume data, thereby generating the maximum pixel value as the maximum intensity projection image.

Further, the image generation unit 1226 can also perform rendering for the volume data, thereby generating the three-dimensional images. Rendering is the processing of two-dimensionally representing the volume data for displaying the volume data on a screen of the display unit 124. For rendering, the shading processing of performing coordinate conversion from three-dimensional coordinates into two-dimensional coordinates of the volume data to provide a stereoscopic effect is performed. Rendering includes, for example, volume rendering and surface rendering.

Figure 7:
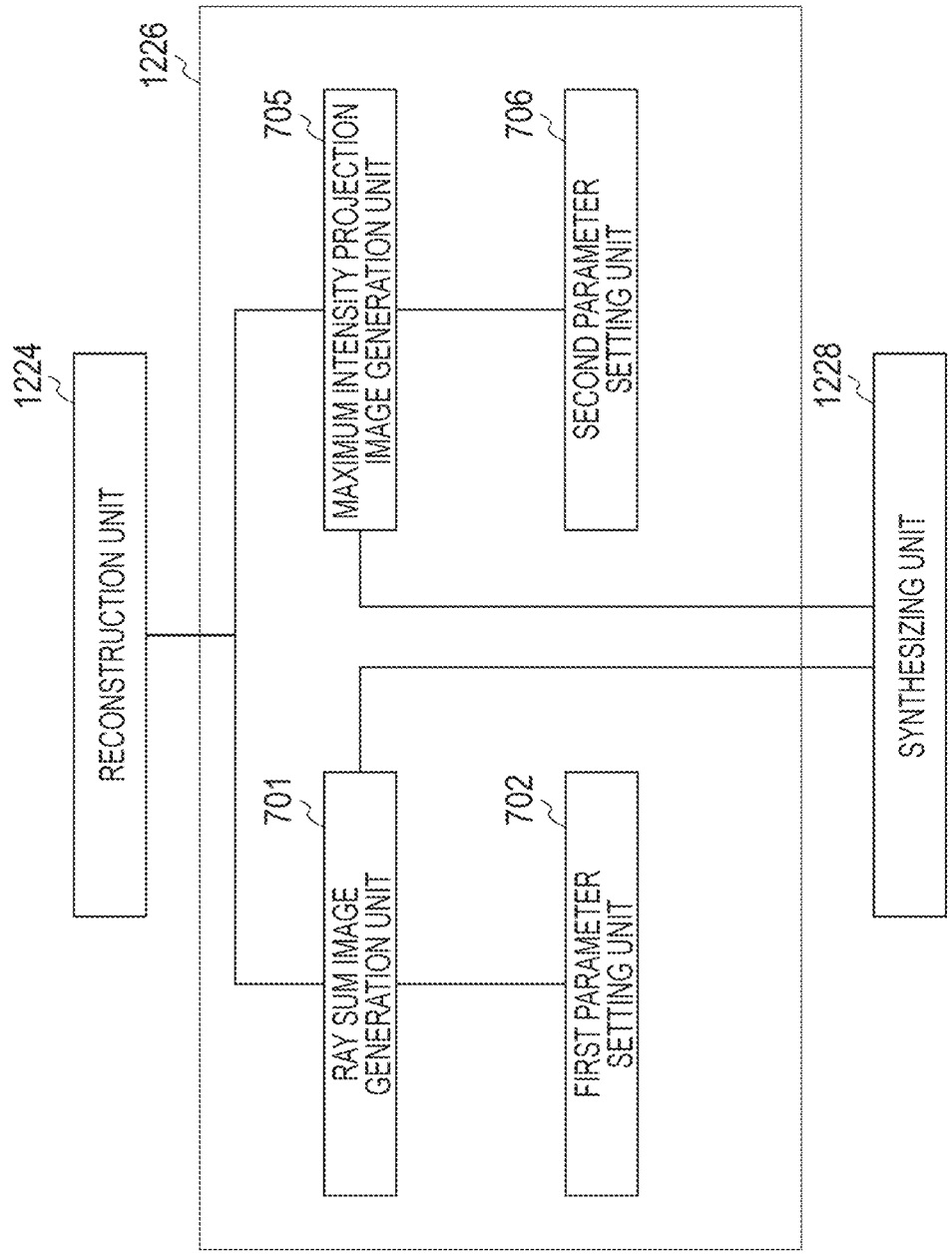
FIG. 7 is a diagram of a configuration of an image generation unit of the present invention.

FIG. 7 illustrates a configuration of the image generation unit 1226. The image generation unit 1226 includes a ray sum image generation unit 701 configured to generate the ray sum image from the volume data, a first parameter setting unit 702 configured to set parameters regarding the ray sum image for the ray sum image generation unit 701, a maximum intensity projection image generation unit 705 configured to generate the maximum intensity projection image from the volume data, and a second parameter setting unit 706 configured to set parameters regarding the maximum intensity projection image for the maximum intensity projection image generation unit 705.

Note that although not shown in the figure, the image generation unit 1226 may include, for example, a rendering unit configured to render the volume data to generate a three-dimensional image, and a minimum value projection image generation unit configured to extract the minimum pixel value in the visual line direction in the volume data to generate the minimum pixel value as a minimum value projection image. That is, the image generation unit 1226 is good enough to generate the multiple types of three-dimensional images.

The ray sum image generation unit 701 generates the ray sum image by means of a ray sum method. The ray sum image generation unit 701 generates, as a projection image, the addition value (the total value) of the pixel values in the visual line direction in the volume data. The ray sum image generation unit 701 adds up all pixel values of the volume data passing through coordinates corresponding to pixels of a projection surface (two-dimensional coordinates) corresponding to the visual line direction, thereby taking such an addition value as a pixel value for the coordinates of the projection surface. The ray sum image generation unit 701 performs similar processing for each coordinate of the projection surface (the two-dimensional coordinates).

The first parameter setting unit 702 sets the visual line direction of the ray sum image generated in the ray sum image generation unit 701. The operator can optionally set the visual line direction (an axial direction, a coronal direction, etc.). In a case where the first parameter setting unit 702 sets the visual line direction of the ray sum image, the second parameter setting unit 706 sets the visual line direction of the maximum intensity projection image to the visual line direction of the ray sum image. That is, the visual line direction of the ray sum image and the visual line direction of the maximum intensity projection image are set to the same direction. For example, when the first parameter setting unit 702 sets the visual line direction of the ray sum image to the axial direction, the second parameter setting unit 706 synchronously sets the visual line direction of the maximum intensity projection image to the axial direction. When the second parameter setting unit 706 sets the visual line direction of the maximum intensity projection image to the coronal direction, the first parameter setting unit 702 synchronously sets the visual line direction of the ray sum image to the coronal direction.

Moreover, the first parameter setting unit 702 sets a window level and a window width of the ray sum image generated in the ray sum image generation unit 701. The first parameter setting unit 702 sets the window level and the window width of the ray sum image so that the ray sum image generation unit 701 can perform setting for gradation processing for the ray sum image. The window level and the window width are parameters for setting a contrasting density (luminance) into which the pixel value of the ray sum image is converted. The pixel value of the ray sum image is, for example, converted into a contrasting density level of 0 to 255. The window level is a center value (a median value) of an image conversion range, and the window width is a value representing the width of the image conversion range.

Figure 8:
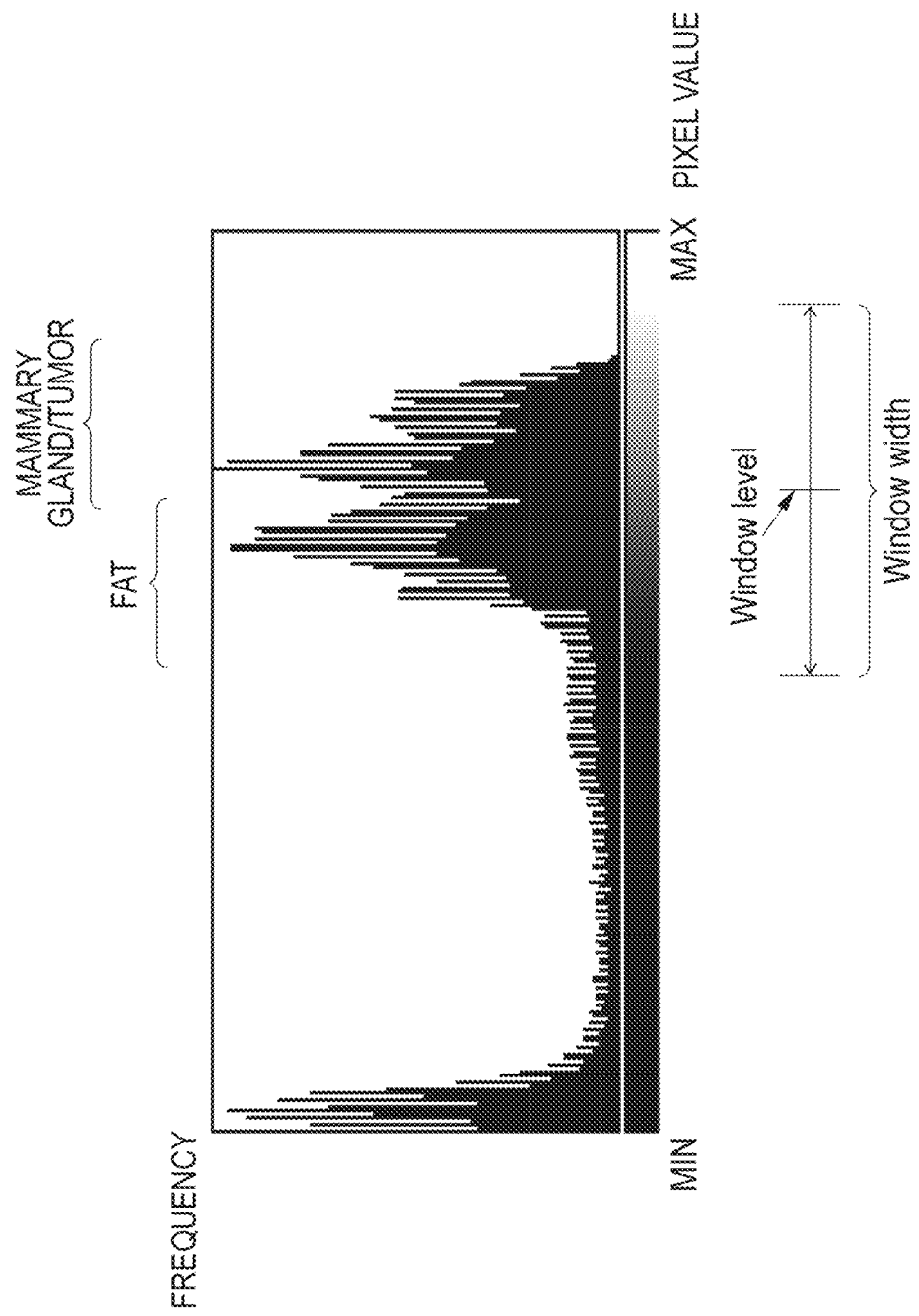
FIG. 8 is a graph of a setting screen for setting a window width and a window level in the present invention.

FIG. 8 shows a setting screen of the first parameter setting unit 702. The setting screen for setting the window level and the window width of the ray sum image is displayed on the display unit 124. Pixel value distribution in the ray sum image generated in the ray sum image generation unit 701 is displayed herein. The display unit 124 displays pixel value distribution of the ray sum image as a histogram. The operator can estimate, from a histogram pattern (a depression-protrusion contour), distribution of pixel values for the fat tissue and the mammary gland/tumor tissue.

The operator can set the window level and the window width corresponding to the histogram of the ray sum image. In FIG. 8, the window width is, for pixel value distribution, set to include distribution of the fat tissue and the mammary gland/tumor tissue. In the case of extracting the pixel values for the mammary gland/tumor tissue, the operator sets, via the first parameter setting unit 702, the window width including distribution of the pixel values for the mammary gland/tumor tissue. The ray sum image generation unit 701 can generate the ray sum image excluding the pixel values for the fat tissue and including the pixel values for the mammary gland/tumor tissue. Thus, the operator can check the mammary gland/tumor tissue from the ray sum image. That is, the first parameter setting unit 702 sets the parameters regarding the ray sum image such that the tumor tissue is visualized in the ray sum image.

Moreover, in FIG. 8, the window level is set between the pixel value for the fat tissue and the pixel value for the mammary gland/tumor tissue. In the case of emphasizing the pixel values for the mammary gland/tumor tissue, the operator sets, via the first parameter setting unit 702, the window level to the center of distribution of the pixel values for the mammary gland/tumor tissue. The ray sum image generation unit 701 can generate the ray sum image with the mammary gland/tumor tissue being emphasized. Thus, the operator can check the mammary gland/tumor tissue by the contrasting density (luminance) of the ray sum image.

Alternatively, the first parameter setting unit 702 can set the range (the three-dimensional region) of the volume data to be projected by the ray sum method. The first parameter setting unit 702 can set the range of the volume data to be projected by the ray sum method such that the range includes the mammary gland/tumor tissue and the periphery thereof.

The maximum intensity projection image generation unit 705 generates the maximum intensity projection image (a MIP image) by means of a maximum intensity projection method (a MIP method). The maximum intensity projection image generation unit 705 selects the maximum pixel value of the volume data passing through the coordinates corresponding to the pixels of the projection surface (the two-dimensional coordinates) corresponding to the visual line direction, thereby taking the maximum value as the pixel value for the coordinates of the projection surface. The maximum intensity projection image generation unit 705 performs similar processing for each coordinate of the projection surface (the two-dimensional coordinates).

The second parameter setting unit 706 sets a window level and a window width of the maximum intensity projection image generated in the maximum intensity projection image generation unit 705. As in the first parameter setting unit 702, a setting screen for setting the window level and the window width of the maximum intensity projection image is displayed on the display unit 124. The window level and the window width are parameters for setting a contrasting density (luminance) into which the pixel value of the maximum intensity projection image is converted. The pixel value of the maximum intensity projection image is, for example, converted into a level of 0 to 255. Pixel value distribution in the maximum intensity projection image generated in the maximum intensity projection image generation unit 705 is extracted herein. The display unit 124 displays pixel value distribution of the maximum intensity projection image as a histogram. The operator sets the window level and the window width corresponding to the histogram of the maximum intensity projection image so that the maximum intensity projection image generation unit 705 can perform gradation processing for the maximum intensity projection image.

Alternatively, the second parameter setting unit 706 can also set the range (the three-dimensional region) of the volume data to be projected by the maximum intensity projection method. The first parameter setting unit 702 and the second parameter setting unit 706 can also set different ranges for the range of the volume data to be projected by the ray sum method and the range of the volume data to be projected by the maximum intensity projection method. For example, the first parameter setting unit 702 and the second parameter setting unit 706 can set the range of the volume data to be projected by the ray sum method broader than the range of the volume data to be projected by the maximum intensity projection method.

The second parameter setting unit 706 can set a threshold regarding the pixel value for visualizing a calcified tissue from the volume data in the maximum intensity projection image. The maximum intensity projection image generation unit 705 uses such characteristics that the pixel values for the periphery of the calcified tissue expand concentrically, thereby visualizing the calcified tissue from the volume data in the maximum intensity projection image.

Figure 9:
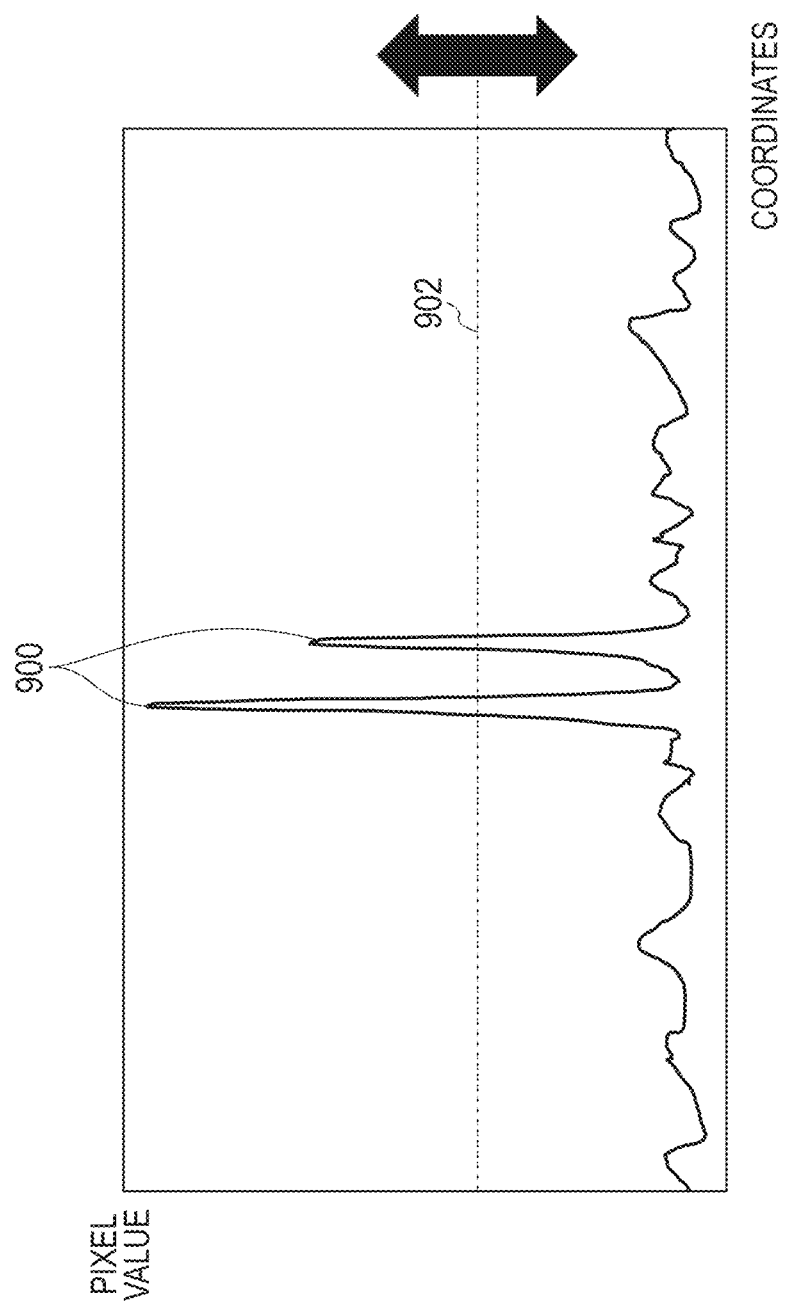
FIG. 9 is a graph of a setting screen for setting a threshold in the present invention.

FIG. 9 illustrates a setting screen for setting a threshold 902 for visualizing the calcified tissue in the maximum intensity projection image. The threshold 902 is illustrated as a dashed line. FIG. 9 shows a profile (distribution) one direction (e.g., an X-direction) in the maximum intensity projection image. The operator can set, via the second parameter setting unit 706, the threshold 902 including pixel values 900 for the calcified tissue. Specifically, the second parameter setting unit 706 moves the threshold 902 in an upper-to-lower direction. The threshold 902 may be set in advance from the characteristics of the pixel value for the calcified tissue. Alternatively, the second parameter setting unit 706 may set, as the threshold, a pixel value corresponding to a predetermined rate (e.g., 50%) from a higher pixel value in pixel value distribution (the histogram) of the maximum intensity projection image.

As described above, the second parameter setting unit 706 sets the threshold 902 for imaging in the maximum intensity projection image. The maximum intensity projection image generation unit 705 selects the maximum pixel value of the volume data passing through the coordinates corresponding to the pixels of the projection surface (the two-dimensional coordinates) corresponding to the visual line direction, the maximum pixel value being equal to or greater than the threshold set by the second parameter setting unit 706. The maximum intensity projection image generation unit 705 takes the selected pixel value as the pixel value for the coordinates of the projection surface. The maximum intensity projection image generation unit 705 does not select a pixel value falling below the threshold set by the second parameter setting unit 706 even when such a pixel value is the maximum pixel value of the volume data passing through the coordinates corresponding to the pixels of the projection surface (the two-dimensional coordinates) corresponding to the visual line direction. In the case of the pixel value falling below the threshold set by the second parameter setting unit 706, the maximum intensity projection image generation unit 705 makes such coordinates of the projection surface transparent. Thus, the maximum intensity projection image generation unit 705 visualizes the calcified tissue from the volume data in the maximum intensity projection image, and does not visualize other tissues than the calcified tissue in the maximum intensity projection image. That is, the second parameter setting unit 706 sets the parameters regarding the maximum intensity projection image such that the calcified tissue is visualized in the maximum intensity projection image.

The synthesizing unit 1228 synthesizes the ray sum image generated in the ray sum image generation unit 701 and the maximum intensity projection image generated in the maximum intensity projection image generation unit 705. Specifically, the synthesizing unit 1228 superimposes the region (the calcified tissue) of the maximum intensity projection image on the ray sum image. Since the region (the calcified tissue) of the maximum intensity projection image is superimposed on the ray sum image, the ray sum image is not displayed in the region (the calcified tissue) of the maximum intensity projection image. That is, displaying is made in preference to the maximum intensity projection image over the ray sum image. Thus, the operator can check the region (the calcified tissue) of the maximum intensity projection image. The region (the calcified tissue) of the maximum intensity projection image is an image including pixel values satisfying the threshold. The ray sum image includes a wide region of the tumor tissue and a peripheral tissue. The maximum intensity projection image includes a local region of the calcified tissue. Thus, a composition image displays the tumor tissue and the peripheral tissue thereof in the ray sum image and the minute calcified tissue in the maximum intensity projection image.

Specifically, the maximum intensity projection image generation unit 705 three-dimensionally calculates the gradient of the pixel value about a relatively-high pixel value position in the volume data. The gradient of the pixel value is used for grasping a situation where the pixel values at the periphery of the calcified tissue expand concentrically. The maximum intensity projection image generation unit 705 extracts the calcified tissue from information on the relatively-high pixel value position and the gradient of the pixel value. With a gentle three-dimensional pixel value gradient at the periphery of the relatively-high pixel value position, the calcified tissue is extracted. Without the gentle three-dimensional pixel value gradient at the periphery of the relatively-high pixel value position, the calcified tissue is not extracted.

The ray sum image generation unit 701 adds up all pixel values of the volume data passing through the coordinates corresponding to the visual line direction and corresponding to the pixels of the projection surface (the two-dimensional coordinates), thereby taking such an addition value as the pixel value for the coordinates of the projection surface. Thus, the ray sum image generation unit 701 generates the ray sum image by means of all pixel values, and therefore, the tissue is not necessarily extracted based on the pixel values.

As described above, the breast imaging device of the present invention includes the image generation unit 1226 configured to generate, from the volume data based on the projection images output from the radiation detection unit, the ray sum image based on the addition value of the pixel values in the visual line direction and the maximum intensity projection image based on the maximum pixel value in the visual line direction, and the synthesizing unit 1228 configured to synthesize the ray sum image and the maximum intensity projection image. Thus, the operator can easily observe each of specific tissues (the tumor tissue and the calcified tissue) from the multiple types of three-dimensional images (the ray sum image and the maximum intensity projection image).

<Display Form>

Figure 10B:
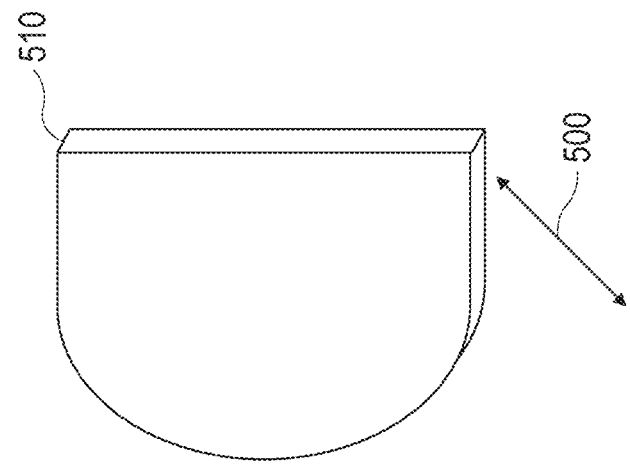
FIGS. 10A and 10B are views of one display form of a display unit of the present invention.
Figure 10A:
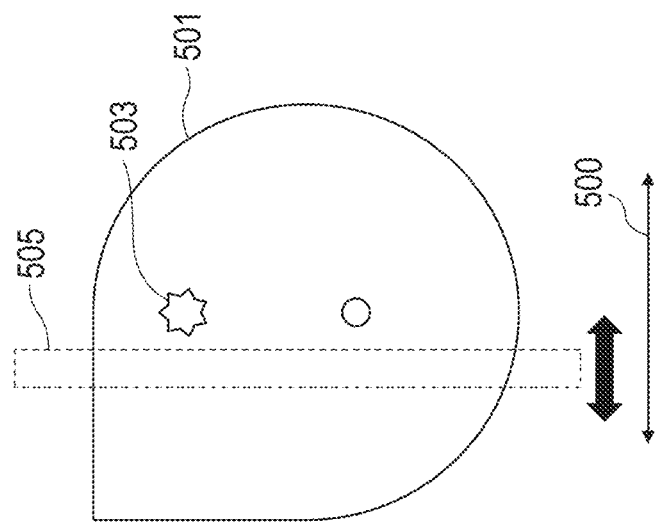

FIGS. 10A and 10B illustrate one display form of the display unit 124. The display unit 124 displays an image 501 for setting the range (the three-dimensional region) of the volume data to be projected and a composition image 510 obtained by synthesizing the ray sum image and the maximum intensity projection image.

FIG. 10A is the image 501 of the entirety of the breast. The image 501 may be an image of a body mark or a three-dimensional image based on the volume data.

The image 501 illustrated in FIG. 10A is an image for setting the range of the volume data to be projected as a projection image. The image 501 illustrated in FIG. 10A includes a tumor tissue 503, but includes no calcified tissue. Thus, the composition image 510 does not include the maximum intensity projection image. The range 505 of the volume data to be projected by the ray sum method is displayed on the image 501. The range 505 of the volume data as described herein is the same as the range of the volume data to be projected by the maximum intensity projection method. The operator sets, via the first parameter setting unit 702, the range 505 of the volume data to be projected by the ray sum method, and sets, via the second parameter setting unit 706, the range 505 of the volume data to be projected by the maximum intensity projection method.

FIG. 10B illustrates the composition image (a superimposed image) 510 of the ray sum image generated based on the addition value of the pixel values in the visual line direction in the range 505 of the volume data and the maximum intensity projection image generated based on the maximum pixel value in the visual line direction in the range 505 of the volume data. The range 505 of the volume data as described herein does not include the tumor tissue and the calcified tissue, and therefore, the composition image does not include the tumor tissue and the calcified tissue. Note that a direction 500 is a right-to-left direction of the image 501 and a depth direction of the composition image 510.

The operator can move, via the first parameter setting unit 702, the range 505 of the volume data to be projected by the ray sum method in an arrow direction (the right-to-left direction). Thus, the range 505 of the volume data can be set such that the ray sum image includes the tumor tissue. Similarly, the operator can move, via the second parameter setting unit 706, the range 505 of the volume data to be projected by the maximum intensity projection method in the arrow direction (the right-to-left direction).

The range 505 of the volume data is movable in the depth direction 500 of an observation region. Moreover, the width of the range 505 of the volume data can be set as necessary.

When the three-dimensional image is generated with thin slices, such an image is useful for observing the tumor tissue and the mammary gland. Moreover, although there are many noise components in the case of a single slice, noise reduction can be realized by generation of the three-dimensional image from the stack of multiple slices, and such a three-dimensional image is useful for recognition of a stereoscopic structure.

Moreover, the pixel values for the tumor tissue and the mammary gland approximate each other in the three-dimensional image, and for this reason, it is difficult to distinguish the tumor tissue from the mammary gland in the case of the thin slices. However, the tumor tissue typically does not include the fat, and therefore, there is a difference in the pixel value between the tumor tissue and the mammary gland in the ray sum image which can be observed with a certain thickness. The range 505 of the volume data is adjusted so that easy distinction between the tumor tissue and the mammary gland can be expected.

FIGS. 11A and 11B illustrate one display form of the display unit 124. The display unit 124 displays the image 501 for setting the range (the three-dimensional region) of the volume data to be projected and the composition image 510 of the ray sum image and the maximum intensity projection image. The operator sets, via the first parameter setting unit 702, the range 505 of the volume data to be projected by the ray sum method, and sets, via the second parameter setting unit 706, the range 505 of the volume data to be projected by the maximum intensity projection method. The range 505 of the volume data as described herein is set to include the tumor tissue 503 in the composition image 510.

FIG. 11B illustrates the composition image (the superimposed image) 510 of the ray sum image generated based on the addition value of the pixel values in the visual line direction in the range 505 of the volume data and the maximum intensity projection image generated based on the maximum pixel value in the visual line direction in the range 505 of the volume data. The image 501 illustrated in FIG. 11A includes the tumor tissue 503, but includes no calcified tissue. Thus, the composition image 510 includes a tumor tissue 503a. The composition image 510 does not include the calcified tissue in the maximum intensity projection image.

Figure 12B:
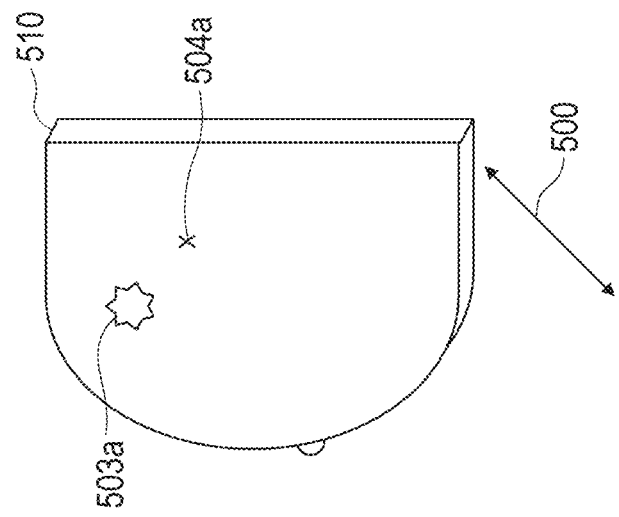
FIGS. 12A and 12B are views of one display form of the display unit of the present invention.
Figure 12A:
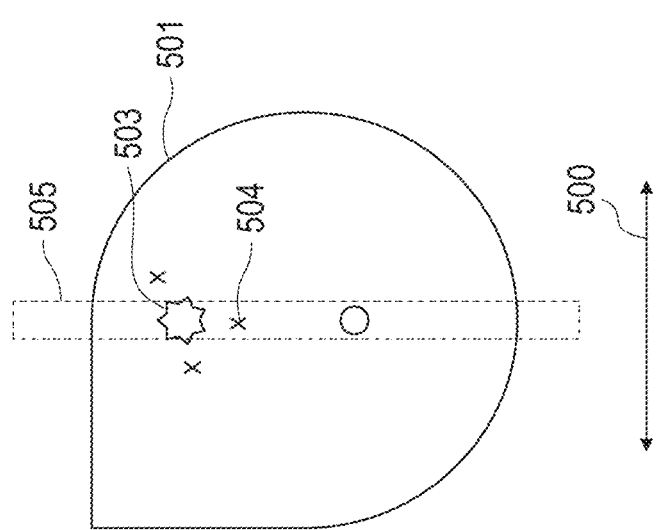

FIGS. 12A and 12B illustrate one display form of the display unit 124. The display unit 124 displays the image 501 for setting the range (the three-dimensional region) of the volume data to be projected and the composition image 510 of the ray sum image and the maximum intensity projection image. The operator sets, via the first parameter setting unit 702, the range 505 of the volume data to be projected by the ray sum method, and sets, via the second parameter setting unit 706, the range 505 of the volume data to be projected by the maximum intensity projection method. The range 505 of the volume data as described herein is set such that the composition image 510 includes the tumor tissue 503 and calcified tissues 504.

FIG. 12B illustrates the composition image (the superimposed image) 510 of the ray sum image generated based on the addition value of the pixel values in the visual line direction in the range 505 of the volume data and the maximum intensity projection image generated based on the maximum pixel value in the visual line direction in the range 505 of the volume data. The range 505 of the volume data as described herein includes the tumor tissue 503 in the ray sum image and the calcified tissues 504 in the maximum intensity projection image, and therefore, the composition image 510 includes the tumor tissue 503a and a calcified tissue 504a.

FIGS. 13A and 13B illustrate one display form of the display unit 124. The display unit 124 displays the image 501 for setting the range (the three-dimensional region) of the volume data to be projected and the composition image 510 of the ray sum image and the maximum intensity projection image. The operator sets, via the first parameter setting unit 702, the range 505 of the volume data to be projected by the ray sum method, and sets, via the second parameter setting unit 706, the range 507 of the volume data to be projected by the maximum intensity projection method. The range 505 of the volume data and the range 507 of the volume data as described herein are set independently.

The operator can set, via the first parameter setting unit 702, the position and width of the range 505 of the volume data to be projected by the ray sum method. The width of the range 505 of the volume data can be set as indicated by an arrow 505a and an arrow 505b.

The operator can set, via the second parameter setting unit 706, the position and width of the range 507 of the volume data to be projected by the maximum intensity projection method. The range 507 of the volume data is set to cover the entirety of the image 501. That is, the range 507 of the volume data is set to the entirety of the volume data. Thus, the calcified tissue can be visualized in the maximum intensity projection image in the entirety of the volume data. The width of the range 507 of the volume data can be set as indicated by an arrow 507a and an arrow 507b.

Note that the image generation unit 1226 can analyze the image 501 for setting the range of the volume data, thereby setting the positions and widths of the range 505 of the volume data and the range 507 of the volume data. An extraction unit (not shown) in the image generation unit 1226 uses such characteristics that the pixel values at the periphery of the calcified tissue expand concentrically, thereby extracting the calcified tissue from the three-dimensional image.

The extraction unit includes, for example, an extraction method using a certain threshold in a three-dimensional image, an extraction method using a local threshold using peripheral pixels, and a method using a ring-shaped filter by means of such a concentration gradient that a pixel value is higher from a peripheral portion of a calcified tissue toward a center portion.

The extraction unit three-dimensionally analyzes the pixel values in the three-dimensional image, thereby specifying the relatively-high pixel value position. Then, the extraction unit three-dimensionally calculates the gradient of the pixel value about the relatively-high pixel value position. The gradient of the pixel value is used for grasping the situation where the pixel values at the periphery of the calcified tissue expand concentrically. The extraction unit extracts the calcified tissue from the information on the relatively-high pixel value position and the gradient of the pixel value.

On the other hand, the tumor tissue is a tissue having a relatively-higher pixel value than those of peripheral tissues and having a greater size than that of the calcified tissue. The extraction unit three-dimensionally analyzes the pixel values in the three-dimensional image, thereby extracting the tumor tissue by means of such characteristics that the tumor tissue has a predetermined size (e.g., equal to or greater than a radius a). The extraction unit extracts, as the tumor tissue, a region having a relatively-higher pixel value than those of peripheral tissues and having a predetermined size (area).

For projecting the tumor tissue and the calcified tissue extracted by the extraction unit, the first parameter setting unit 702 sets the position and width of the range 505 of the volume data such that the range 505 of the volume data includes the tumor tissue. Moreover, the second parameter setting unit 706 sets the position and width of the range 507 of the volume data such that the range 507 of the volume data includes the calcified tissue.

FIG. 13B illustrates the composition image (the superimposed image) 510 of the ray sum image generated based on the addition value of the pixel values in the visual line direction in the range 505 of the volume data and the maximum intensity projection image generated based on the maximum pixel value in the visual line direction in the range 505 of the volume data. The range 505 of the volume data as described herein includes the tumor tissue 503 in the ray sum image, and the range 507 of the volume data includes the multiple calcified tissues 504. Thus, the composition image 510 includes the tumor tissue 503a and the calcified tissues 504a.

As described above, the multiple types of three-dimensional images are superimposed at the same position, and therefore, the three-dimensional image can be displayed without positional deviation of structures with different characteristics, such as the tumor tissue and the calcified tissue.

Note that in the composition image 510, superimposition on the ray sum image may be performed with a concentration corresponding to the pixel value of the maximum intensity projection image of the calcified tissue 504 being set. Superimposition on the ray sum image may be performed with a transmittance corresponding to the pixel value of the maximum intensity projection image of the calcified tissue 504 being set.

When multiple images are superimposed, a transparency parameter may be set for a single image or multiple images. For example, the transparency parameter may be set based on the concentration of each pixel of the maximum intensity projection image representing minute calcification. In the case of extracting minute calcification, the transparency parameter may be set using the size etc. of such calcification as a parameter.

The display unit 124 may display a three-dimensional image of a single breast, or may display, for comparison, three-dimensional images of the simultaneously-imaged right and left breasts of the subject. Alternatively, the display unit 124 may display, for comparison, three-dimensional images of the same portion imaged previously or imaged for another subject.

The image processing device (the image processing unit 122) of the present invention includes the image generation unit configured to generate, from the volume data, the ray sum image based on the addition value of the pixel values in the visual line direction and the maximum intensity projection image based on the maximum pixel value in the visual line direction, the synthesizing unit configured to synthesize the ray sum image and the maximum intensity projection image, and a display control unit (not shown) configured to cause the display unit 124 to display the composition image.

A computer program for implementing the functions of the above-described embodiment can be supplied to a computer via a network or a storage medium (not shown), and then, can be executed. That is, the computer program is a program for implementing the functions of the image processing device by the computer. The storage medium stores the computer program.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-179105, filed Sep. 19, 2017, which is hereby incorporated by reference herein in its entirety.

What is claimed is:

1. A breast imaging device for rotating a radiation detection unit configured to detect radiation irradiated from a radiation generation unit configured to generate the radiation with the radiation detection unit and the radiation generation unit facing each other, comprising:
    a ray sum image generation unit configured to generate a ray sum image based on an addition value of at least one pixel value in a visual line direction from volume data reconstructed from a projection image output from the radiation detection unit;
    a maximum intensity projection image generation unit configured to generate a maximum intensity projection image based on a maximum pixel value in the visual line direction from the volume data;
    a synthesizing unit configured to synthesize the ray sum image and the maximum intensity projection image;
    a first parameter setting unit configured to set a parameter regarding the ray sum image for the ray sum image generation unit; and
    a second parameter setting unit configured to set a parameter regarding the maximum intensity projection image for the maximum intensity projection image generation unit, wherein
    the first parameter setting unit sets the parameter regarding the ray sum image such that a tumor tissue is visualized in the ray sum image, and
    the second parameter setting unit sets the parameter regarding the maximum intensity projection image such that a calcified tissue is visualized in the maximum intensity projection image.

2. The breast imaging device according to claim 1, wherein the first parameter setting unit sets a range of the volume data to be projected by a ray sum method.

3. The breast imaging device according to claim 1, wherein the second parameter setting unit sets a range of the volume data to be projected by a maximum intensity projection method.

4. The breast imaging device according to claim 1, wherein the first parameter setting unit and the second parameter setting unit set different ranges as the range of the volume data to be projected by a ray sum method and the range of the volume data to be projected by a maximum intensity projection method.

5. The breast imaging device according to claim 4, wherein the first parameter setting unit and the second parameter setting unit set the range of the volume data to be projected by the ray sum method broader than the range of the volume data to be projected by the maximum intensity projection method.

6. The breast imaging device according to claim 1, wherein the second parameter setting unit sets a threshold regarding the pixel value for visualizing the calcified tissue from the volume data in the maximum intensity projection image.

7. The breast imaging device according to claim 6, wherein the maximum intensity projection image generation unit selects the maximum pixel value of the volume data corresponding to the visual line direction and being equal to or greater than the threshold, thereby generating the maximum intensity projection image.

8. The breast imaging device according to claim 1, wherein the visual line direction of the ray sum image and the visual line direction of the maximum intensity projection image are set to be an identical direction.

9. The breast imaging device according to claim 1, wherein the maximum intensity projection image is superimposed on the ray sum image.

10. An image processing device comprising:
- a ray sum image generation unit configured to generate a ray sum image based on an addition value of at least one pixel value in a visual line direction from volume data;
- a maximum intensity projection image generation unit configured to generate a maximum intensity projection image based on a maximum pixel value in the visual line direction from the volume data;
- a synthesizing unit configured to synthesize the ray sum image and the maximum intensity projection image;
- a first parameter setting unit configured to set a parameter regarding the ray sum image for the ray sum image generation unit; and
- a second parameter setting unit configured to set a parameter regarding the maximum intensity projection image for the maximum intensity projection image generation unit, wherein the first parameter setting unit sets the parameter regarding the ray sum image such that a tumor tissue is visualized in the ray sum image, and the second parameter setting unit sets the parameter regarding the maximum intensity projection image such that a calcified tissue is visualized in the maximum intensity projection image.

11. An image processing method comprising:

generating a ray sum image based on an addition value of at least one pixel value in a visual line direction from volume data;

generating a maximum intensity projection image based on a maximum pixel value in the visual line direction from the volume data;

synthesizing the ray sum image and the maximum intensity projection image;

a first parameter setting unit configured to set a parameter regarding the ray sum image for the ray sum image generation unit; and a second parameter setting unit configured to set a parameter regarding the maximum intensity projection image for the maximum intensity projection image generation unit, wherein the first parameter setting unit sets the parameter regarding the ray sum image such that a tumor tissue is visualized in the ray sum image, and the second parameter setting unit sets the parameter regarding the maximum intensity projection image such that a calcified tissue is visualized in the maximum intensity projection image.

* * * * *